United States Patent [19]
Hildebrand et al.

[11] Patent Number: 5,940,802
[45] Date of Patent: Aug. 17, 1999

[54] DIGITAL DISEASE MANAGEMENT SYSTEM

[75] Inventors: P. Lloyd Hildebrand; Stephen R. Fransen, both of Edmond; Gene M. Soderstrom Hopper, Oklahoma City, all of Okla.

[73] Assignee: The Board of Regents of the University of Oklahoma, Norman, Okla.

[21] Appl. No.: 08/819,157

[22] Filed: Mar. 17, 1997

[51] Int. Cl.$^6$ .................................................. G06F 159/00
[52] U.S. Cl. .................................................. 705/3
[58] Field of Search ....................................... 705/1, 3, 4

[56] References Cited

U.S. PATENT DOCUMENTS

| | | |
|---|---|---|
| 3,566,370 | 2/1971 | Worthington . |
| 4,722,349 | 2/1988 | Baumberg . |
| 4,974,607 | 12/1990 | Miwa . |
| 5,099,424 | 3/1992 | Schneiderman ............... 364/413.02 |
| 5,339,821 | 8/1994 | Fujimoto . |
| 5,421,343 | 6/1995 | Feng . |
| 5,462,051 | 10/1995 | Oka et al. . |
| 5,473,537 | 12/1995 | Glazer et al. ....................... 128/630 |
| 5,482,043 | 1/1996 | Zulauf . |
| 5,544,649 | 8/1996 | David et al. ........................ 128/630 |
| 5,633,910 | 5/1997 | Cohen .................................. 379/38 |
| 5,722,418 | 3/1998 | Bro ..................................... 128/732 |
| 5,724,968 | 3/1998 | Diff .................................... 128/630 |

OTHER PUBLICATIONS

"Is Disease Management Good Therapy. . .", 7 pages, by William G. Castagnoli, Internet printout, date Sep. 1994.
"Disease Management Shows Great Promise", 3 pages, Internet printout, date Dec. 14, 1995.
"The Disease Management Evolution", pharmatech, by Matthew B. Wiener, 2 pages, Internet printout, date 1996.

*Primary Examiner*—Frantzy Poinvil
*Attorney, Agent, or Firm*—Dunlap, Codding & Rogers

[57] ABSTRACT

A method for improving the delivery of health care for patients. A first data signal being multimedia data which is indicative of a patient condition of a selected patient is input into a local computer. Clinical data, cost data and administrative data relating to the health of the selected patient are also input into the local computer. The first data signal is combined with the clinical data, cost data and administrative data to form a first patient information signal which is transmitted to a central computer. A predetermined disease stage is then assigned to the selected patient based on the first data signal. The disease stage is combined with the first patient information signal to form a second patient information signal. Then, a first array of risk factors is computed from a database containing a plurality of previously obtained individualized patient information records. A first predictive probability is then assigned to the selected patient based on the second patient information signal and the first array of risk factors. A first patient recommendation signal indicating one of the selected patient would benefit from immediate patient care and the selected patient would not benefit from immediate patient care is generated and then transmitted to the local computer. Both the second patient information signal and the first patient recommendation signal are transmitted to a regional computer in response to the first patient recommendation signal indicating that the selected patient requires immediate patient care.

16 Claims, 1 Drawing Sheet

DIGITAL DISEASE MANAGEMENT SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates generally to devices and methods for improving the delivery of patient care to patients, and more particularly, but not by way of limitation to devices and methods for improving the delivery of patient care to patients wherein patient information relating to a selected patient is obtained at a local facility system and is automatically transmitted to a regional facility system in response to a first patient recommendation signal indicating that the selected patient would benefit from immediate patient care.

2. Brief Description of the Related Art

About sixteen million people in the United States are diabetics. It is known in the art that diabetics are at risk for a disease referred to as "diabetic retinopathy". Diabetic retinopathy is an insidious disease which if left untreated may cause blindness or serious vision loss. Because diabetic retinopathy does not cause pain or a change in the appearance of an afflicted individual's eye, diabetics afflicted with diabetic retinopathy are typically unaware of a condition that threatens their vision. About 40,000 of the sixteen million diabetics in the United States may go blind each year because of unsuspected and untreated diabetic retinopathy.

Although not all of these 40,000 diabetics can be effectively treated to prevent blindness even with regular screening eye exams, we estimate that blindness could be prevented in about 50% of these 40,000 diabetics if all of such diabetics were regularly screened for diabetic retinopathy. It should be noted that most general physicians are either untrained or lack the necessary equipment to detect diabetic retinopathy through an eye exam. Thus, diabetics must typically be examined by an optometrist or an ophthalmologist, some of whom are retinal specialists, on a regular basis so that diabetic retinopathy can be detected in its early stages.

However, there are many barriers to health care such as time, money, and convenience which prevent diabetics from receiving regular screening eye-exams. For example, ophthalmologists and retinal specialists are typically located in urban areas while diabetics are located in both urban areas and rural areas. Thus, it has been difficult for the diabetics living in rural areas to obtain the necessary regular eye exams from optometrists, ophthalmologists or retinal specialists because of the time and travel commitments needed for diabetics living in rural areas. In addition, there are access problems involved in diabetics receiving regular screening eye exams even for those who live near comprehensive medical facilities. That is, diabetics should regularly have data collected about their eyes, their kidneys, their feet and their nervous system, for example. Currently, diabetics must have a separate appointment with an optometrist or ophthalmologist to have their eyes examined, and a separate appointment with a nephrologist for kidney evaluation, and a separate appointment with a podiatrist to have their feet examined, and a separate appointment with a neurologist to have their nervous system examined, etc. This creates problems for both the diabetic patient and the health care providers in that it is inconvenient for the diabetic patient and difficult for each of the health care providers to keep each other informed. For these and possibly other reasons It has been estimated that only about 50% of diabetics participate in regular screening eye exams.

In addition to the loss of sight of diabetics, unsuspected and untreated diabetic retinopathy is also costly to society. Substantial savings on society which result from the screening for diabetic retinopathy have been predicted by several computer models. All of the models are based on estimates of the annual cost of diagnosing and treating diabetic retinopathy, the annual cost of a year of blindness to the federal government, the effectiveness of treatment and data depicting the prevalence, incidence and progression of the disease. Relying on the sum of annual Social Security benefits, Social Security insurance, tax losses and payments from Medicare and Medicaid, the savings to society per individual successfully enrolled in a long-term screening and treatment program amounts to about $9571 per year.

To this end, a need has long existed for a disease management system that increases the accuracy and accessibility of health care while also reducing the expenses incurred thereby. It is to such a system that the present invention is directed.

DETAILED DESCRIPTION OF THE INVENTION

Figure 1:
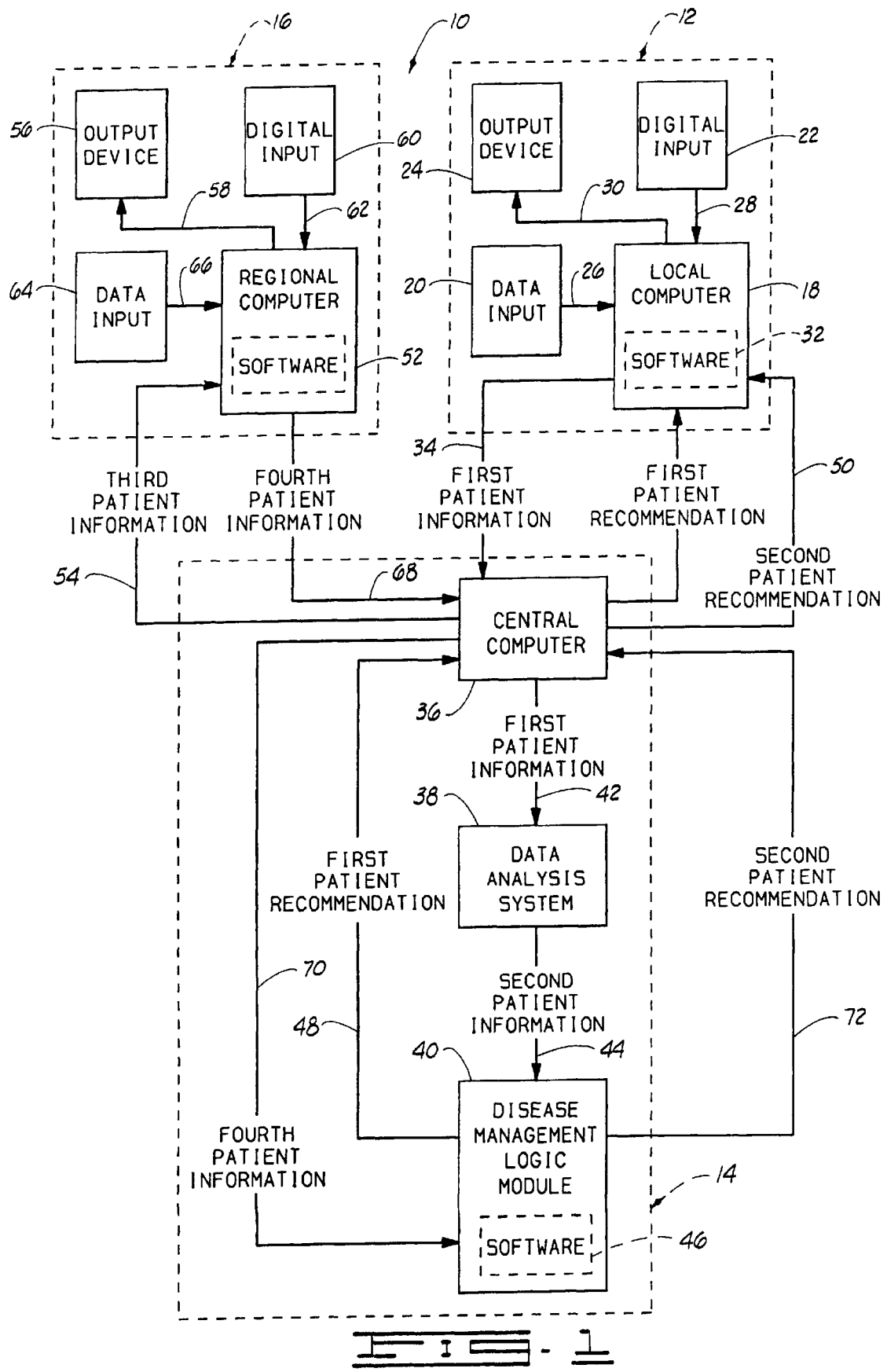
FIG. 1 is a schematic, diagrammatic view of a digital disease management system for improving the delivery of health care to patients which is operating in accordance with the present invention.

The term "patient" as used herein alone or in combination with other words includes patients, clients, residents and consumers, and in general means a person receiving health care.

The term "patient condition" as used herein means an abnormal or diseased state of part of the patient's body. For example, the patient condition can be diabetic retinopathy, dermatologic lesions, glaucoma or any other patient condition where clinical data parameters can be converted into digital information and subsequently transmitted.

The term "health care provider" as used herein means a doctor, a technician, a nurse or any other person who directly or indirectly delivers health care to a patient. For example, if the patient condition is diabetic retinopathy, the health care provider is typically an optometrist or an ophthalmologist some of whom are retinal specialists.

The term "multimedia data" as used herein refers to any type of data or information which is indicative of any patient condition of a selected patient or patients. For example, the multimedia data can be composed of still or animated images, sounds, text, binary or analog data and combinations thereof.

The terms "internet" and/or "signal path" refers to any suitable communication link which permits electronic communications. It should be understood that the term "internet" is not limited to "the Internet" or any other particular system or type of communication link. That is, the terms "internet" and/or "signal path" are intended only to refer to any suitable communication system, including extra-computer system and intra-computer system communications. Examples of such communications systems include internal busses, local area networks, wide area networks, point-to-point shared and dedicated communications, infra-red links, microwave links, telephone links, CATV links, satellite and radio links and fibre-optic links. The terms "internet" and/or "signal path" can also refer to any suitable communication system for sending messages between remote locations, directly or via a third party communication provider such as AT&T. In this instance, messages can be communicated via telephone or facsimile or computer synthesized voice telephone messages with or without voice or tone recognition, or any other suitable communications technique.

The terms "immediate" or "immediate patient care" as used herein typically mean that the patient should receive patient care within 90 days, and desirably within about 30 days of the current diagnosis when the disease condition is diabetic retinopathy. However, it should be understood that the terms "immediate" or "immediate patient care" as used herein can refer to any length of time from diagnosis so long as the disease stage of the selected patient is not expected to progress significantly during this time period.

The terms "would not benefit from immediate patient care" as used herein is not intended to mean that the selected patient does not benefit from or need patient care entirely, but is intended to means that it is expected, recommended or more cost effective that the selected patient not receive treatment before the selected patient is screened again. For example, if it is expected that the patient condition of a selected patient may improve with no medical intervention or that the patient condition will not progress significantly in a length of time greater than the period between regular screenings, the present system may indicate that the selected patient "would not benefit from immediate patient care" to indicate that no medical intervention should be initiated before the next regular screening or that another screening exam should be scheduled to more closely monitor the progression of the patient condition.

It should be understood that each of the signal paths are shown and described separately herein for the sole purpose of clearly illustrating the information being communicated between each of the individual components of the present invention. In operation, the signal paths may not be separate signal paths but may be a single signal path.

Shown in FIG. 1 and indicated by the general reference numeral 10 is a digital disease management system for improving the delivery of health care to patients which is constructed in accordance with the present invention. The system 10 is provided with a plurality of local facility systems 12, a plurality of central facility systems 14 and a plurality of regional facility systems 16. Only one of the local facility systems 12, the central facility systems 14 and the regional facility systems 16 are shown in FIG. 1 for purposes of clarity.

Each of the local facility systems 12 can be located at a local treatment facility which is positioned anywhere that is convenient or accessible for the selected patient, such as at the selected patient's home or in a health care provider's office where a selected patient presents to receive a check-up, examination, physical or the like. The central facility systems 14 are typically located in a central reading center which is disposed remotely from the local facility system 12 and it is envisioned that the central facility systems 14 will be located at or near an urban area or medical research institute where it is likely that medical specialists will reside.

In one embodiment of the present invention, each of the central facility systems 14 will be adapted to recommend treatment concerning one or more different patient conditions. Each of the regional facility systems 16 are typically located in a regional treatment center. The regional treatment centers are typically located in geographically disparate locations from the local facility systems 12 so that a centrally located regional treatment center is located near some of the local facility systems 12 so that patients initially presenting at local facility systems 12 near the centrally located regional treatment center will be referred to the centrally located regional treatment center for purposes of convenience. The regional treatment center can be any treatment center, such as a doctor's office or a hospital, where specialized equipment is used to provide health care for a patient.

However, it should be understood that the local facility systems 12, regional facility systems 16 and the central facility systems 14 do not have to be disposed in geographically disparate locations. For example, the local facility systems 12, regional facility systems 16 and the central facility systems 14 of the digital disease management system 10 could be located within one building, such as a multi-specialty clinic, where health care providers (such as ophthalmologists) have access to specialized equipment (such as laser surgery capabilities) to provide comprehensive patient or health care to patients.

It should also be understood that although each of the local facility systems 12, regional facility systems 16 and central facility systems 14 are described as separate entities herein, the hardware and software of the local facility systems 12, regional facility systems 16 and central facility systems 14 could be implemented as a single computer system or a plurality of interconnected computer systems, or a general purpose computer system, or a distributed processing system, all of which are well understood in the art.

The operation of the system 10 will be generally described herein with respect to a specific patient condition referred to as "diabetic retinopathy". However, it will be understood that such operation applies equally with respect to various other categories or types of patient conditions.

The local facility system 12 is provided with a local computer 18 which is connected to a data input device 20, a digital input device 22 and an output device 24 as indicated by the signal paths 26, 28, and 30, respectively. The local computer 18 can be any suitable computer or patient monitor. For example, the local computer 18 can be a Macintosh PowerPC which is obtainable from Apple Computers, Inc.

The local computer 18 receives a first data signal from the digital input device 22 via the signal path 28. The first data signal can be any digital or multimedia data which is composed of clinical data and which is indicative of any patient condition of a selected patient and the digital input device 22 is any suitable device for obtaining such digital multimedia data. For example, if the patient condition is diabetic retinopathy, the first data signal is typically a digitized fundus image of the eye of the selected patient and the digital input device 22 is a stereoscopic digital camera, such as a DCS digital camera which is obtainable from Kodak coupled with a fundus camera which is obtainable from Zeiss; and if the patient condition is glaucoma, the first data signal is typically digitized intraocular pressures and the digital input device 22 is any suitable piece of equipment for obtaining and digitizing such intraocular pressures.

Once received by the local computer 18, the first data signal is output over the signal path 30 to be received by the output device 24. The output device 24 can be any suitable output device such as a printer or a monitor. If the output device 24 is a monitor the first data signal can be displayed by the monitor as a patient "album" which displays rows and columns of individual frames of data. A still image of the first data signal can be displayed as a thumbnail of the full resolution image while a video clip of the first data signal can be represented by a frozen frame introducing the video clip with controls to play the video clip.

The local computer 18 receives a second data signal relating to the health of the selected patient from the data input device 20. The second data signal received from the data input device 20 can be any desirable patient data related to the selected patient, such as additional clinical data, cost data and administrative data. The data input device 20 can be a personal digital assistant, or a keyboard, for example.

The clinical data can be any clinical data relating to the health or patient condition of the selected patient. For example, if the patient condition is diabetic retinopathy, the clinical data can be visual acuity data, diastolic blood pressure data, amount of insulin data, type of diet data, hemoglobin A1C levels data, age data, or data relating to length of time in which the selected patient has had diabetes.

The cost data can be any cost data relating to the health or patient condition of the selected patient. Typically, the cost data can be generated using activity based costing parameters designated by the financially responsible organization's (for example an insurance company, health maintenance organization, integrated health delivery system, or a group practice) accounting system. For example, groups of cost data can be direct costs, indirect costs and allocated costs, while categories of cost data include personnel costs, equipment costs, depreciation costs, general and administrative costs and supplies costs.

The administrative data can be any suitable administrative data relating to the health or patient condition of the selected patient. For example, the administrative data can be patient demographics data, payor of patient expenses data, scheduling data, health system data and data relating to which physicians are performing the management of the patient condition of the selected patient.

The local computer 18 is loaded with a software program 32 which receives the first data signal and the second data signal and which combines the first data signal with the second data signal to form a first patient information signal relating to the health of the selected patient. The first patient information signal is transmitted by the local computer 18 over a signal path 34 to be received by one of the central facility systems 14 which is capable of recommending treatment relating to the appropriate patient condition of the selected patient. If data is being collected at the local facility system 12 concerning more than one type of patient condition or more than one type of test concerning the same patient condition, the local facility system 12 may transmit one first patient information signal relating to one of the types of patient conditions or test types to the appropriate central facility system 14 which is capable of recommending treatment for that particular patient condition or test type, and another first patient information signal to another appropriate central facility system 14 which is capable of recommending treatment for that other particular patient condition or test type. For example, the digital disease management system 10 may have one central facility system 14 which is capable of recommending treatment for eye exams (diabetic retinopathy) and another central facility system 14 which is capable of recommending treatment for nervous systems. In this example, the selected patient presents to one local facility system 12 and has eye exam data collected and input into the local computer 18 and nervous system data collected and input into the local computer 18. The local computer 18 would then transmit one first patient information signal to one of the central facility systems 14 specializing in eye exams and another first patient information signal to another one of the central facility systems 14 specializing in nervous systems, or the local facility system 12 would send one first patient information signal containing information regarding both of the patient conditions or test types to one central facility system 14 if that central facility system 14 is capable of recommending treatment for both patient conditions or test types.

It should be noted that the data input device 20 and the digital input device 22 have been described herein as separate components to clarify the types of data received by the local facility system 12. Thus, it should be understood that in use, the local facility system 12 may be provided with either one or both of the data input device 20 and the digital input device 22.

Each central facility system 14 is provided with a central computer 36, a data analysis system 38 and a disease management logic module (DMLM) 40. Although the central computer 36, data analysis system 38, and the disease management logic module 40 are shown and described separately herein it should be understood that this is solely for purposes of clarity. Thus, the central computer 36, data analysis system 38, and the disease management logic module 40 can be one integrated system, or two or more separate systems.

The first patient information signal is received and stored by the central computer 36 of the central facility system 14. The central computer 36 can be any suitable computer, such as a "PowerPC Macintosh" which is obtainable from Apple computers. Once the first patient information signal is stored by the central computer 36, the first patient information signal is transmitted to the data analysis system 38 via a signal path 42.

The data analysis system 38 receives and stores the first patient information signal, and in response thereto, the data analysis system 38 assigns a predetermined disease stage to the selected patient based on the data contained in the first data signal component of the first patient information signal. The disease stages are determined by the clinical features of the patient condition.

For example, if the patient condition is diabetic retinopathy, the specific features of the clinical data (digital images of the eye) to be analyzed include: macular edema (accumulation of fluid in the retina), microaneurysms, retinal hemorrhages, retinal exudates (accumulation of lipid and protein in the retina), cotton wool patches (areas of retinal infarction), venous beading, intraretinal microvascular abnormalities (patterns of growth of irregular vessels in the retina), neovascularization (patterns of irregular vessels growing out of the retina), vitreous hemorrhage, retinal traction and retinal detachment. These patient characteristics allow classification of the patient condition into the following disease stages.

| | |
|---|---|
| Class 1 | Normal or minimal nonproliferative diabetic retinopathy |
| Class 2 | Nonproliferative diabetic retinopathy without macular edema |

| | |
|---|---|
| Class 3 | Nonproliferative diabetic retinopathy with macular edema that is not clinically significant |
| Class 4 | Nonproliferative diabetic retinopathy with clinically significant macular edema (CSME) |
| Class 5 | Severe nonproliferative diabetic retinopathy (preproliferative) |
| Class 6 | Non-high-risk proliferative diabetic retinopathy |
| Class 7 | Non-high-risk proliferative diabetic retinopathy with CSME |
| Class 8 | High-risk proliferative diabetic retinopathy |
| Class 9 | High-risk proliferative diabetic retinopathy not amenable to photocoagulation |

Preferred Practice Pattern: Diabetic Retinopathy, American Academy of Ophthalmology, 1993.

The data analysis system 38 can be either manual or electronic and the signal path 42 can be either manual or electronic. For example, if the data analysis system 38 is manual, the data analysis system 38 may comprise health care providers which view the first data signal (digital images of the eye) at the central computer 36 and then assign a predetermined disease stage to the selected patient based on the first data signal. However, if the data analysis system 38 is electronic, the data analysis system 38 can comprise a computer loaded with software which analyzes the first data signal and then automatically assigns a predetermined disease stage to the selected patient based on the first data signal.

The disease stage assigned to the selected patient is input into the central computer 36 and combined with the first patient information signal to form a second patient information signal relating to the health of the selected patient. The second patient information signal is transmitted to the disease management logic module 40 via a signal path 44. The signal path 44 can be either manual or electronic. For example, when the signal path 44 is manual, such signal path 44 may be people typing the disease stage and the first patient information signal into a computer comprising the disease management logic module 40, and when the signal path 44 is electronic, the signal path 44 may be a local area network or the internal bus of the computer.

The disease management logic module 40 receives the second patient information signal. The disease management logic module 40 is provided with a database 46 containing a plurality of previously obtained individualized patient information records. Each of the previously obtained patient information records desirably contain patient information relating to the patient care of an individual patient. For example, the patient information stored in each of the individualized patient information records could contain such information as the clinical data, cost data, administrative data, and disease stage data which is included in the second patient information signal; and treatment parameter data which will be described hereinafter.

The disease management logic module 40 builds predictive models of patient condition outcomes and patient condition progressions utilizing the information contained in the database 46. With respect to diabetic retinopathy, each of the individualized patient information records contain at least four parameters which have been linked as "comorbid" conditions and thereby affect the rate of progression of the disease or patient condition. These four parameters are: 1) length of diabetes; 2) age of patient; 3) mean HbA1C levels; and 4) the presence of microalbuminuric.

The disease management logic module 40 utilizes the information contained in the database 46 to categorize the selected patient into a population with similar characteristics and to quantify, compute or build a first array of relative risk factors from population statistics which are generally predictive of the progression of the patient condition or disease of the selected patient over a given period of time given that selected patient's particular array of "comorbid" conditions. Once the first array of relative risk factors is computed, the disease management logic module 40 utilizes the first array of relative risk factors and the disease stage assigned by the data analysis system 38 to assign a first predictive probability to the selected patient. The first predictive probability indicates whether or not the selected patient is inflicted with the patient condition, and if the selected patient is inflicted with the patient condition, the first predictive probability also indicates the probability that the patient condition of the selected patient will advance or progress to a higher disease stage (e.g., from class 1 to class 2) within a relatively short period of time.

In one embodiment, the disease management logic module 40 computes the first predictive probability by assigning the selected patient to a cell in a multidimensional transitional probability table containing the first array of relative risk factors and predetermined disease stages or experiences of a population of patients having identical or similar characteristics as the selected patient.

The disease management logic module 40 then matches or compares the selected patient's patient characteristics (e.g. the disease stage assigned to the selected patient by the data analysis system 38, the administrative data and the clinical data relating to the selected patient) with the population of patients (whose information is contained in the database) that share substantially similar patient characteristics to provide an indication (the first predictive probability) of the probability of the disease progression of the patient condition of the selected patient.

The disease management logic module 40 then generates a first patient recommendation signal based on the first predictive probability. The first patient recommendation signal provides a predictive model of a preferred or recommended treatment for the selected patient's patient condition. It should be noted that optimal treatment recommendations will be generated in the first patient recommendation signal by the disease management logic module 40 based on linking disease management logic module optimal management options with the cost of those options through predictive cost models. For example, if a patient has a near threshold condition (i.e. very close to needing laser surgery or is in a high risk group for vision loss) the cost of increasing screening activities in this patient (screening more often, for example) may offset the cost of potential vision loss or early surgery, and therefore be a better way to manage the patient medically and economically.

The disease management logic module 40 is typically provided with both electronic and manual components. That is, the database 46 is typically maintained on a computer, such as the central computer 36, and the first array of relative risk factors, the predictive models and cost models are typically computed by the computer given the information discussed above. However, the recommending of one of the predictive models and cost models in the first patient recommendation signal as the recommended treatment may be accomplished by a human health care provider who recommends one of the predictive and cost models after reviewing such models and then enters or inputs such recommendations into the computer.

The first patient recommendation signal typically includes the disease stage assigned by the data analysis system 38 and the first predictive probability. Typically, the predictive model of the first patient recommendation signal is in the form of a recommended timed schedule which indicates whether or not the selected patient would benefit from immediate patient care (medical intervention) or would not benefit from immediate patient care.

If the first predictive probability indicates that there is a high probability that the patient condition will advance or progress to a higher disease stage within a relatively short period of time, the first patient recommendation signal will indicate that the selected patient would benefit from immediate patient care, such as laser photocoagulation surgery, via a recommended schedule. In this case, the first patient recommendation schedule will indicate that an appointment needs to be scheduled for the selected patient at one of the regional treatment centers which can provide treatment concerning the patient condition.

If, however, the first predictive probability indicates that the selected patient is not inflicted with the patient condition or that there is a low probability that the patient condition will advance or progress to a higher disease stage within a relatively short period of time, the first patient recommendation signal will indicate that the selected patient would not benefit from immediate patient care (surgery, for example) but needs to be screened again via a predetermined time schedule of every three months, for example. In this case, the first patient recommendation signal will indicate that an appointment needs to be scheduled for the selected patient to present again at the local facility system 12 within the predetermined time.

For example, a 53 year male old patient with non-insulin dependent diabetes mellitus (NIDDM) and uncontrolled hypertension (mean diastolic blood pressure of 120) and three consecutive urinalyses demonstrating microalbuminuric over the last three months with a 20 year history of diabetes and with nonproliferative diabetic retinopathy and non-clinically significant macular edema (class 3 disease stage) presents on initial evaluation to the digital disease management system 10. In this case, the first predictive probability may demonstrate a 0.5% chance of progression to disease stage 4 in three months, a 7.0% chance of progression to disease stage 4 in six months, and a 25.0% chance of progression to disease stage 4 in nine months. Given these probabilities, the first patient recommendation signal would recommend that the selected patient would not benefit from immediate patient care but needs to be screened again in three months. If the selected patient presents with similar findings at the three month follow-up visit a similar risk and patient recommendation would be allocated to the selected patient. However, if the selected patient had increased to the class 4 disease stage then the first patient recommendation signal would indicate that the selected patient would benefit from immediate patient care so that laser surgery could be delivered before significant visual loss occurs. The specific known risks or comorbid factors contributing to disease progression are her age, length of time the patient has had diabetes, elevated blood pressure, and early evidence of kidney problems (albumin in the urine).

It should be noted that the database 46 will be initially provided with an incomplete array of transitional probabilities because such database 46 will be provided with information obtained through the existing global experience as documented in multiple clinical trials. However, by incorporating the actual experiences of patients, such as the selected patient, which are managed by the system 10 into the database 46, the risk probabilities such as the first array of relative risk factors and/or the array of transitional probabilities will be progressively influenced by actual experience from within the system 10. Thus, the patient information such as the information contained in the second information signal is used to update the database 46.

The central facility system 14 can be programmed to provide a notification to the selected patient if the selected patient does not receive another screening exam at the appropriate time. For example, assume that the local facility system 12 is located at the selected patient's home and the selected patient is supposed to be examined or provide care for himself once a day and the data collected by such examination (the first patient information signal) is provided to one of the central facility systems 14 by the local facility system 12 on a daily basis. In this case, if the one central facility system 14 does not receive information from the local facility system 12 after a predetermined time of two days, for example, the central facility system 14 may output a notification signal to alert a health care provider that the selected patient is not receiving daily exams.

The disease management logic module 40 transmits the first patient recommendation signal to the central computer 36 via a signal path 48. The central computer 36 receives the first patient recommendation signal, and in response thereto, the central computer 36 transmits the first patient recommendation signal to the local computer 18 via a signal path 50.

The local computer 18 receives the first patient recommendation signal, and in response thereto, the local computer 18 outputs the first patient recommendation signal to the output device 24 so that the first patient recommendation signal is perceivable by a health care provider.

In response to the first patient recommendation signal indicating that the selected patient would benefit from immediate patient care, the central computer 36 automatically or manually transmits a third patient information signal to a regional computer 52 located at the regional facility system 16 via a signal path 54. The third patient information signal is typically indicative of both the second patient information signal and the first patient recommendation signal. However, it should be understood that the third patient information signal can be a signal notifying the regional facility system 16 that information is available to such regional facility system 16 so that the regional computer 52 can retrieve the information contained in the second patient information signal and/or the first patient recommendation signal when appropriate so that such information can be utilized in the treatment of the selected patient. In addition, it should be understood that an appointment schedule of the selected patient may be either transmitted to or made available to the regional facility system 16 by the central facility system 14.

The regional computer 52 receives the third patient information signal, and in response thereto, the regional computer 52 outputs the third patient information signal to an output device 56 via a signal path 58 such that the information relating to the selected patient which is contained within the third patient information signal is perceivable by a health care provider located at the regional treatment center so that the information contained in the third patient information signal can be utilized by the health care provider to render individualized patient care (e.g. laser photocoagulation) to the selected patient in accordance with the third patient information signal. The regional computer 52 can be any suitable computer, such as a Macintosh PowerPC which is obtainable from Apple Computers, Inc.

Please note that at the time of treatment, the patient diagnosis is already established (thus, no screening exam is required), and the diagnostic information (e.g. digital photographs and clinical data) is available to the health care provider so that the treatment of the selected patient can proceed efficiently.

Once health or patient care is rendered to the selected patient, post-operative patient care data is input into the regional computer in the form of a third data signal transmitted by a digital input device 60 via a signal path 62. For example, if the patient condition is diabetic retinopathy, the third data signal is typically a digitized fundus image of the eye of the patient photographed after patient care has been rendered to the selected patient and the digital input device 60 is a stereoscopic digital camera, such as a DCS digital camera which is obtainable from Kodak coupled to a fundus camera which is obtainable from Zeiss; and if the patient condition is glaucoma, the third data signal is typically digitized intraocular pressures and the digital input device 60 is any appropriate input device which is capable of obtaining and digitizing such pressures.

Once received by the regional computer 52, the third data signal is output over the signal path to be received by the output device 56. The output device 56 can be any suitable output device such as a printer or a monitor. If the output device 56 is a monitor the third data signal can be displayed by the monitor as a patient "album" which displays rows and columns of individual frames of data. A still image of the first data signal can be displayed as a thumbnail of the full resolution image while a video clip of the first data signal can be represented by a frozen frame introducing the video clip with controls to play the video clip.

The regional computer 52 receives a fourth data signal relating to the post-treatment health of the selected patient from a data input device 64 via a signal path 66. The fourth data signal received from the data input device 64 can be any desirable post-treatment or pre-treatment patient related data, such as treatment parameters data and follow-up recommendations data. With respect to the patient condition being diabetic retinopathy, the treatment parameters typically include: date, diagnosis, eye treated, number of laser applications, laser spot size, laser power duration, laser wavelength, method of anesthesia, complications and area (s) of treatment.

The third data signal and the fourth data signal are combined by the regional computer 52 to form a fourth patient information signal relating to the post-treatment health of the selected patient. The fourth patient information signal is transmitted to the central computer 36 from the regional computer 52 via a signal path 68.

It should be noted that the data input device 64 and the digital input device 60 have been described herein as separate components to clarify the types of data received by the regional treatment system 16. It should be understood that in use, the regional treatment system 16 may be provided with either one or both of the digital input device 60 and the data input device 64.

The fourth patient information signal is received by the central computer 36, and in response thereto, the central computer 36 transmits the fourth patient information signal to the disease management logic module 40 via a signal path 70. The fourth patient information signal is received by the disease management logic module 40.

The disease management logic module 40 then utilizes the treatment parameter data contained in the fourth patient information signal to update the database 46 of the disease management logic module 40 so that experiences or information learned from the rendering of health or patient care to the selected patient can be utilized by the disease management logic module 40 as feedback to track the progress of the patient condition of the selected patient so that the predictive probabilities determined by the disease management logic module 40 can become increasingly more accurate. In other words, the database 46 is updated so that the experiences, treatment recommendations and progress of the selected patient can be used to provide predictive probabilities for other patients.

Once the database 46 of the disease management logic module 40 is updated, the updated database 46 is utilized by the disease management logic module 40 to compute or build a second array of relative risk factors which are generally predictive of the progression of the patient condition or disease of a patient. Once the second array of relative risk factors is computed, the disease management logic module 40 utilizes the second array of relative risk factors, the disease stage assigned by the data analysis system 38 and the clinical data contained in the fourth patient information signal to assign a second predictive probability to the selected patient in a similar manner as the first predictive probability was assigned to the selected patient as hereinbefore described. That is, the second predictive probability indicates whether or not the selected patient is inflicted with the patient condition, and if the selected patient is inflicted with the patient condition, the second predictive probability also indicates the probability that the patient condition of the selected patient will advance or progress to a higher disease stage (e.g., from class 1 to class 2) within a relatively short period of time.

In other words, the disease management logic module 40 matches or compares the selected patient's patient characteristics (the disease stage assigned to the selected patient by the data analysis system 38 and the clinical data relating to the selected patient) with a population of patients (whose information is contained in the database) that share substantially similar patient characteristics to provide an indication (the second predictive probability) of the probability of the disease progression of the patient condition of the selected patient.

The disease management logic module 40 then generates a second patient recommendation signal based on the second predictive probability in a similar manner as the first patient recommendation signal was generated, as hereinbefore described. That is, the second patient recommendation signal provides a predictive model of a preferred or recommended treatment for the selected patient's patient condition. It should be noted that optimal treatment recommendations will be generated in the second patient recommendation signal by the disease management logic module 40 based on linking disease management logic module optimal management options with the cost of those options through predictive cost models.

The second patient recommendation signal typically includes the disease stage assigned by the data analysis system 38 and the second predictive probability. Typically, the predictive model of the second patient recommendation signal is in the form of a recommended timed schedule which indicates whether or not the selected patient would benefit from immediate patient care (medical intervention) or would not benefit from immediate patient care.

If the second predictive probability indicates that there is a high probability that the patient condition will advance or progress to a higher disease stage within a relatively short period of time, the second patient recommendation signal will indicate that the selected patient would benefit from immediate patient care, such as laser photocoagulation surgery, via a recommended schedule. In this case, the second patient recommendation schedule will indicate that an appointment needs to be scheduled for the selected patient at one of the regional treatment centers.

If, however, the second predictive probability indicates that the selected patient is not inflicted with the patient condition or that there is a low probability that the patient condition will advance or progress to a higher disease stage within a relatively short period of time, the second patient recommendation signal will indicate that the selected patient would not benefit from immediate patient care (surgery, for example) but needs to be screened again via a predetermined time schedule of every three months, for example. In this case, the second patient recommendation signal will indicate that an appointment needs to be scheduled for the selected patient to present again at the local facility system 12 within the predetermined time.

The disease management logic module 40 transmits the second patient recommendation signal to the central computer 36 via a signal path 72. The central computer 36 receives the second patient recommendation signal, and in response thereto, the central computer 36 transmits the second patient recommendation signal to the local computer 18.

The local computer 18 receives the second patient recommendation signal, and in response thereto, the local computer 18 outputs the second patient recommendation signal to the output device 24 so that the second patient recommendation signal is perceivable by a patient care provider.

While only one cycle of each process or method disclosed herein has been described in detail, it should be understood that the processes or methods disclosed herein are designed to be repeated for any one of a number of predetermined times so that the digital disease management system 10 can be utilized continuously by patients and health care providers as provided herein.

Changes may be made in the steps or the sequence of steps of the methods described herein without departing from the spirit and the scope of the invention as defined in the following claims.

What is claimed is:

1. A method for improving the delivery of health care for patients, comprising the steps of:
   a. receiving a first patient information signal by a central facility computer, the first patient information signal being related to a selected patient and composed of multimedia data selected from the group comprising clinical data, cost data, administrative data, and combinations thereof;
   b. assigning one of a plurality of predetermined disease stages to the selected patient based on information contained in the first patient information signal;
   c. inputting the predetermined disease stage into the central facility computer;
   d. assigning a first predictive probability to the selected patient by the central facility computer based on at least one of the first patient information signal, the disease stage and a first array of risk factors, the first array of risk factors being computed from a database containing a plurality of previously obtained individualized patient information records, each of the patient information records containing patient information relating to the patient care of an individual patient;
   e. inputting the first predictive probability into the central facility computer;
   f. generating a first patient recommendation signal by the central facility computer, the first patient recommendation signal indicating a recommendation selected from the group of recommendations comprising the selected patient would benefit from immediate patient care and the selected patient would not benefit from immediate patient care;
   g. transmitting the first patient recommendation signal to a local computer;
   h. receiving the first patient recommendation signal by the local computer; and
   i. transmitting, from the central facility computer to a regional computer located at a regional treatment center, a second patient information signal in response to the first patient recommendation signal indicating that the selected patient would benefit from immediate patient care.

2. A method, as recited in claim 1, further comprising the step of:
   j. rendering individualized patient care to the selected patient at the regional treatment center in accordance with the information contained in the second patient information signal.

3. A method, as recited in claim 2, further comprising the steps of:
   k. transmitting, by the regional computer, a third patient information signal relating to the post-treatment health of the selected patient to the central facility, the third patient information signal being multimedia data which is selected from the group comprising clinical data, cost data, treatment parameter data, administrative data, and combinations thereof;
   l. receiving the third patient information signal by the central facility computer; and
   m. updating the database with at least the treatment parameter data contained within the third patient information signal.

4. A method, as recited in claim 3, further comprising the steps of:
   n. computing a second array of risk factors from the updated database;
   o. assigning a second predictive probability to the selected patient based on the information contained in the third patient information signal and the second array of risk factors;
   p. inputting the second predictive probability into the central facility computer; and
   q. generating, by the central facility computer, a second patient recommendation signal indicating a recommendation selected from the group of recommendations comprising the selected patient would benefit from immediate patient care and the selected patient would not benefit from immediate patient care.

5. A method, as recited in claim 1, wherein the first patient information signal is transmitted by the local computer to the central facility computer.

6. A method for improving the delivery of health care for patients, comprising the steps of:
   a. receiving a first patient information signal by a central facility computer, the first patient information signal being related to a selected patient and composed of multimedia data selected from the group comprising clinical data, cost data, administrative data, and combinations thereof;
   b. assigning one of a plurality of predetermined disease stages to the selected patient based on information contained in the first patient information signal;

c. inputting the predetermined disease stage into the central facility computer;
d. assigning a first predictive probability to the selected patient by the central facility computer based on at least one of the first patient information signal, the disease stage and a first array of risk factors, the first array of risk factors being computed from a database containing a plurality of previously obtained individualized patient information records, each of the patient information records containing patient information relating to the patient care of an individual patient;
e. inputting the first predictive probability into the central facility computer;
f. generating a first patient recommendation signal by the central facility computer, the first patient recommendation signal indicating a recommendation selected from the group of recommendations comprising the selected patient would benefit from immediate patient care and the selected patient would not benefit from immediate patient care;
g. transmitting the first patient recommendation signal to a local computer;
h. receiving the first patient recommendation signal by the local computer; and
i. transmitting, from at least one of the central facility computer and the local computer to a regional computer located at a regional treatment center, a second patient information signal in response to the first patient recommendation signal indicating that the selected patient would benefit from immediate patient care.

7. A method, as recited in claim 6, further comprising the step of:
j. rendering individualized patient care to the selected patient at the regional treatment center in accordance with the information contained in the second patient information signal.

8. A method, as recited in claim 7, further comprising the steps of:
k. transmitting, by the regional computer, a third patient information signal relating to the post-treatment health of the selected patient to the central facility computer, the third patient information signal being multimedia data which is selected from the group comprising clinical data, cost data, treatment parameter data, administrative data, and combinations thereof;
l. receiving the third patient information signal by the central facility computer; and
m. updating the database with at least the treatment parameter data contained within the third patient information signal.

9. A method, as recited in claim 8, further comprising the steps of:
n. computing a second array of risk factors from the updated database;
o. assigning a second predictive probability to the selected patient based on the information contained in the third patient information signal and the second array of risk factors;
p. inputting the second predictive probability into the central facility computer; and
q. generating a second patient recommendation signal indicating a recommendation selected from the group of recommendations comprising the selected patient would benefit from immediate patient care and the selected patient would not benefit from immediate patient care.

10. A method, as recited in claim 6, wherein the first patient information signal is transmitted by the local computer to the central facility computer.

11. A method for improving the delivery of health care for patients, comprising the steps of:
a. receiving a first patient information signal relating to the health of a selected patient by a central facility computer, the first patient information signal being composed of multimedia data selected from the group comprising clinical data, cost data, administrative data, and combinations thereof, the clinical data being selected from the group of data comprising images of the selected patient's eye, visual acuity, diastolic blood pressure, amount of insulin, type of diet, hemoglobin A1C levels, age, and length of time in which the selected patient has had diabetes, the cost data being selected from the group of data comprising personnel cost, equipment cost, depreciation cost, general and administrative costs and supplies cost, the administrative data being selected from the group of data comprising demographics, payer, scheduling, health system and which specialty physicians are managing the patient's diabetes and complications of diabetes;
b. assigning one of a plurality of predetermined disease stages to the selected patient based on the clinical data contained in the first patient information signal;
c. inputting the predetermined disease stage into the central facility computer;
d. computing a first array of risk factors from a database containing a plurality of previously obtained individualized patient information records, each of the patient information records containing patient information relating to the patient care of an individual patient;
e. assigning a first predictive probability to the selected patient based on the information contained in the first patient information signal, the predetermined disease stage and the first array of risk factors;
f. inputting the first predictive probability into the central facility computer;
g. generating a first patient recommendation signal by the central facility computer, the first patient recommendation signal indicating a recommendation selected from the group of recommendations comprising the selected patient would benefit from immediate patient care and the selected patient would not benefit from immediate patient care;
h. transmitting the first patient recommendation signal to a local computer located at a local treatment facility;
i. receiving the first patient recommendation signal by the local computer; and
j. transmitting a second patient information signal to a regional computer located at a regional treatment center in response to the first patient recommendation signal indicating that the selected patient would benefit from immediate patient care.

12. A method, as recited in claim 11, wherein the second patient information signal is composed of the first patient information signal, the predetermined disease stage and the first patient recommendation signal and wherein the method further comprises the step of:
k. rendering individualized patient care to the eye of the selected patient at the regional treatment center in accordance with the information contained in the second patient information signal.

13. A method, as recited in claim 12, further comprising the steps of:

l. transmitting, by the regional computer, a third patient information signal to the central facility computer, the third patient information signal being composed of multimedia data selected from the group comprising clinical data and treatment parameter data relating to the post-treatment health of the selected patient, the treatment parameter data being selected from the group of data comprising date, diagnosis, eye treated, number of laser applications, laser spot size, laser power duration, laser wavelength, method of anesthesia, complications, area(s) of treatment, and combinations thereof;

m. receiving the third patient information signal by the central facility computer; and n. updating the database with at least some of the treatment parameter data contained within the third patient information signal.

14. A method, as recited in claim 13, further comprising the steps of:

o. computing a second array of risk factors from the updated database by the central facility computer;

p. assigning a second predictive probability to the selected patient based on the third patient information signal and the second array of risk factors;

q. inputting the second predictive probability into the central facility computer; and r. generating a second patient recommendation signal by the central facility computer, the second patient recommendation signal indicating a recommendation selected from a group of recommendations comprising the selected patient would benefit from immediate patient care and the selected patient would not benefit from immediate patient care.

15. A method, as recited in claim 11, further including the step of:

s. photographing the eye of the selected patient with a stereoscopic digital camera to provide a digitized image of the eye of the selected patient.

16. A method for improving the delivery of health care delivered to a selected patient, comprising the steps of:

a. photographing, at a local facility, the eye of a selected patient with a stereoscopic digital camera to provide clinical data composed of a first digitized image of the eye of the selected patient;

b. inputting, automatically, the first digitized image of the eye of the selected patient into a local computer which is located at the local facility;

c. inputting cost data, administrative data and additional clinical data relating to the health of the selected patient and the treatment of diabetic retinopathy into the local computer, the clinical data being selected from the group of data comprising visual acuity, diastolic blood pressure, amount of insulin, type of diet, hemoglobin A1C levels, age, length of time in which the selected patient has had diabetes, and combinations thereof, the cost data being selected from the group of data comprising personnel cost, equipment cost, depreciation cost, general and administrative costs, supplies cost, and combinations thereof, the administrative data being selected from the group of data comprising demographics, payer, scheduling, health system and which specialty physicians are managing the patient's diabetes, complications of diabetes, and combinations thereof;

d. combining, by the local computer, the first digitized image of the eye of the selected patient with the clinical data, cost data and administrative data to form a first patient information signal relating to the treatment of diabetic retinopathy of the selected patient;

e. transmitting, by the local computer, the first patient information signal to a central computer which is located at a central information center, the central information center being located remotely from the local computer;

f. receiving and storing, by the central computer, the first patient information signal;

g. transmitting, by the central computer, the first patient information signal to a data analysis system;

h. receiving, by the data analysis system, the first patient information signal;

i. assigning, by the data analysis system, a predetermined disease stage relating to diabetic retinopathy to the selected patient based on the first digitized image of the eye;

j. combining the disease stage with the first patient information signal to form a second patient information signal;

k. transmitting the second patient information signal to a disease management logic module;

l. receiving by the disease management logic module the second patient information signal;

m. computing a first array of risk factors by the disease management logic module, the first array of risk factors being selected from the group of risk factors comprising age, length of diabetes, diastolic blood pressure, HbA1C levels and combinations thereof from a database containing a plurality of previously obtained individualized patient information records, each of the patient information records containing patient information relating to the patient care of diabetic retinopathy of an individual patient;

n. assigning a first predictive probability to the selected patient based on the second patient information signal and the first array of risk factors;

o. inputting the first predictive probability into the disease management logic module;

p. generating a first patient recommendation signal based on the first predictive probability by the disease management logic module, the first patient recommendation signal including the disease stage assigned by the data analysis system, the first predictive probability and a predictive model of an individualized preferred treatment of diabetic retinopathy, the preferred treatment indicating a recommendation selected from a group of recommendations comprising the selected patient would benefit from immediate patient care and the selected patient would not benefit from immediate patient care;

q. transmitting the first patient recommendation signal from the disease management logic module to the central computer;

r. receiving the first patient recommendation signal by the central computer;

s. transmitting the first patient recommendation signal to the local computer;

t. receiving the first patient recommendation signal by the local computer;

u. outputting via the local computer the first patient recommendation signal to an output device such that the first patient recommendation signal is perceivable by a patient care provider;

v. transmitting, automatically, a third patient information signal indicative of both the second patient information signal and the first patient recommendation signal by the central computer to a regional computer located at a regional treatment center in response to the first patient recommendation signal indicating that the selected patient would benefit from immediate patient care, the regional treatment center being located remotely from the local facility;

w. receiving the third patient information signal by the regional computer;

x. outputting via the regional computer the third patient information signal to an output device such that the information relating to the selected patient which is contained within the third patient information signal is perceivable by a patient care provider located at the regional treatment center;

y. rendering individualized patient care to the selected patient in accordance with the third patient information signal;

z. photographing, at the regional treatment center, the eye of the selected patient with a stereoscopic digital camera after care has been rendered to the selected patient to provide a second digitized image of the eye of the selected patient;

aa. inputting, automatically, the second digitized image of the eye of the selected patient into the regional computer;

ab. inputting treatment parameters relating to the post-treatment health of the selected patient into the local computer, the treatment parameters being selected from a group comprising date, diagnosis, eye treated, number of laser applications, laser spot size, laser power duration, laser wavelength, method of anesthesia, complications, area(s) of treatment, and combinations thereof;

ac. combining, by the local computer, the second digitized image of the eye of the selected patient with the treatment parameter data to form a fourth patient information signal;

ad. transmitting the fourth patient information signal to the central computer from the regional computer;

ae. receiving the fourth patient information signal by the central computer;

af. transmitting the fourth patient information signal to the disease management logic module;

ag. receiving the fourth patient information signal by the disease management logic module;

ah. updating the database of the disease management logic module with the clinical data contained within the fourth patient information signal;

ai. computing a second array of risk factors from the updated database;

aj. assigning a second predictive probability to the selected patient based on the fourth patient information signal and the second array of risk factors;

ak. inputting the second predictive probability into the disease management logic module;

al. generating a second patient recommendation signal indicating a recommendation selected from a group of recommendations consisting of the selected patient would benefit from follow up patient care and the selected patient would not benefit from follow up patient care;

am. transmitting the second patient recommendation signal from the disease management logic module to the central computer;

an. receiving the second patient recommendation signal by the central computer; and ao. transmitting the second patient recommendation signal to the local computer.

* * * * *

UNITED STATES PATENT AND TRADEMARK OFFICE
CERTIFICATE OF CORRECTION

PATENT NO. : 5,940,802  
DATED : August 17, 1999  
INVENTOR(S) : P. Lloyd Hildebrand et al.

It is certified that error appears in the above-identified patent and that said Letters Patent is hereby corrected as shown below:

Drawings,
Replace FIG. 1 with new drawing.

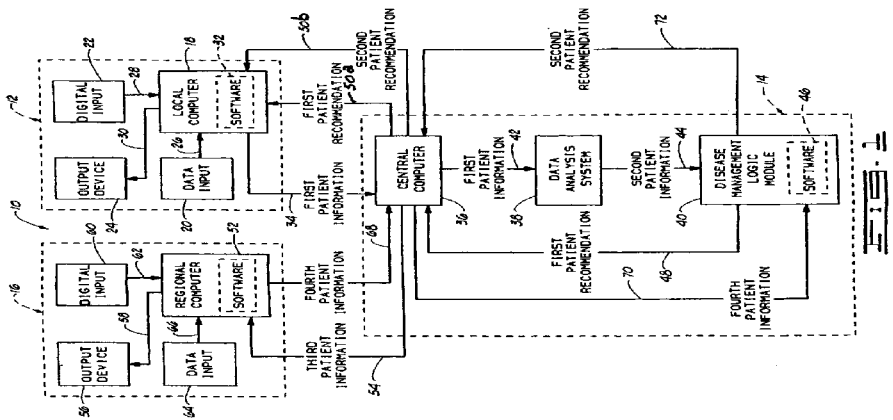

Column 2,
Line 3, delete "It" and substitute therefor -- it --.

Column 3,
Line 40, delete "are" and substitute therefor -- is --.

Column 4,
Line 4, delete "are" and substitute therefor -- is --.
Line 30, delete "are" and substitute therefor -- is --.
Line 45, after "by" and before "signal" delete "the".

Column 7,
Line 50, delete "contain" and substitute -- contains -- therefor.
Line 62, delete "contain" and substitute -- contains -- therefor.

Column 8,
Line 61, delete "the recommending of" and substitute -- recommending -- therefor.

UNITED STATES PATENT AND TRADEMARK OFFICE
CERTIFICATE OF CORRECTION

PATENT NO.    : 5,940,802
DATED         : August 17, 1999
INVENTOR(S)   : P. Lloyd Hildebrand et al.

It is certified that error appears in the above-identified patent and that said Letters Patent is hereby corrected as shown below:

<u>Column 9,</u>
Line 33, delete "male old" and substitute -- old male -- therefor.

<u>Column 10,</u>
Line 28, delete "50" and substitute therefor -- 50a --.

<u>Column 13,</u>
Line 24, after "signal" and before "to" insert -- via signal path 50b --.

Signed and Sealed this

Eleventh Day of February, 2003

JAMES E. ROGAN
*Director of the United States Patent and Trademark Office*